(12) United States Patent
Kreidler et al.

(10) Patent No.: US 8,590,724 B2
(45) Date of Patent: Nov. 26, 2013

(54) LOCK FOR STERILIZATION CONTAINER

(75) Inventors: Winfried Kreidler, Tuttlingen (DE); Jochen Kreidler, Tuttlingen (DE)

(73) Assignee: Innovations Medical GmbH, Tuttlingen (DE)

( * ) Notice: Subject to any disclaimer, the term of this patent is extended or adjusted under 35 U.S.C. 154(b) by 0 days.

(21) Appl. No.: 13/586,929

(22) Filed: Aug. 16, 2012

(65) Prior Publication Data
US 2013/0043250 A1 Feb. 21, 2013

(30) Foreign Application Priority Data

Aug. 17, 2011 (DE) .................... 20 2011 104 615 U

(51) Int. Cl.
*B65D 45/20* (2006.01)
*B65D 45/24* (2006.01)

(52) U.S. Cl.
USPC ........................... 220/324; 220/4.22; 292/246

(58) Field of Classification Search
USPC .................. 220/324, 326, 4.22; 292/246, 247
See application file for complete search history.

(56) References Cited

U.S. PATENT DOCUMENTS

| 460,437 | A | * | 9/1891 | Grove | 292/247 |
|---|---|---|---|---|---|
| 2,559,681 | A | * | 7/1951 | Senseman | 292/250 |
| 4,035,009 | A | * | 7/1977 | Jacobs | 292/246 |
| 4,111,476 | A | * | 9/1978 | Jacobs | 292/246 |
| 4,331,251 | A | | 5/1982 | Berman et al. | |
| 4,818,502 | A | * | 4/1989 | Taschner | 422/310 |
| 4,915,913 | A | | 4/1990 | Williams et al. | |
| 5,725,428 | A | * | 3/1998 | Achmuller | 463/20 |
| 6,371,326 | B1 | * | 4/2002 | Gabele et al. | 220/326 |
| 6,955,381 | B2 | * | 10/2005 | Parker et al. | 292/113 |
| 7,370,891 | B1 | * | 5/2008 | Schmitt et al. | 292/113 |
| 7,540,364 | B2 | * | 6/2009 | Sanderson | 190/119 |
| 2002/0162841 | A1 | * | 11/2002 | Shamir et al. | 220/326 |

FOREIGN PATENT DOCUMENTS

DE 721 588 C 6/1942
DE 197 55 532 A1 6/1999

* cited by examiner

*Primary Examiner* — Mickey Yu
*Assistant Examiner* — Niki Eloshway
(74) *Attorney, Agent, or Firm* — McGlew and Tuttle, P.C.

(57) ABSTRACT

A lock for locking a sterilization container has box-like bottom part and a container cover that can be removed and placed airtightly and connected on the bottom part by a seal to form a closed sterilization space. The lock has a tensioning lever pivotable into an opened position, and a closing flap rotatable about an axis of rotation, with a positive-locking closed position with the tensioning lever. The tensioning lever is able to be brought via the closing flap, during the rotary motion of the closing flap into an opened rotated position, with the closing flap disengaged from the tensioning lever after a further rotary motion into a fully opened end position. The tensioning lever may be fixed in open, and the closing flap positive-lockingly engages with the tensioning lever during closing and the tensioning lever is able be to moved into a closed tensioned position by the closing flap.

10 Claims, 3 Drawing Sheets

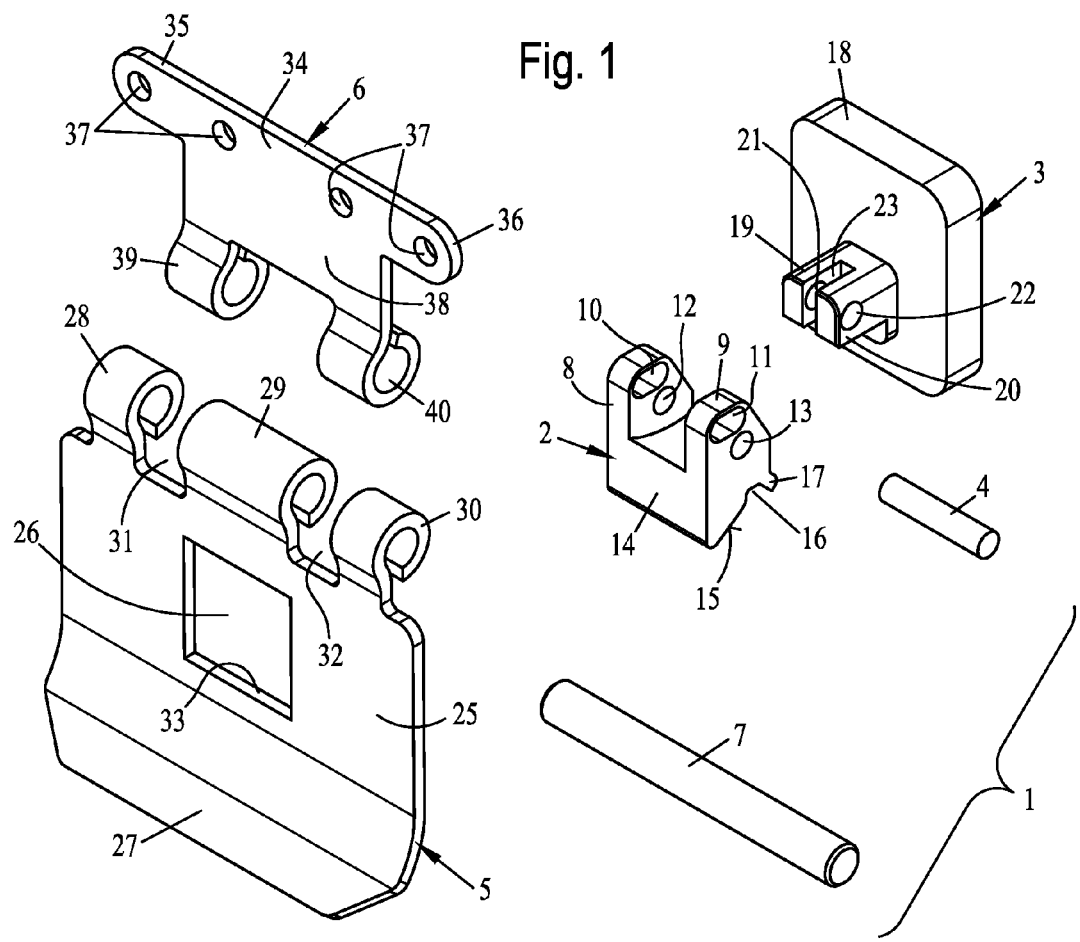
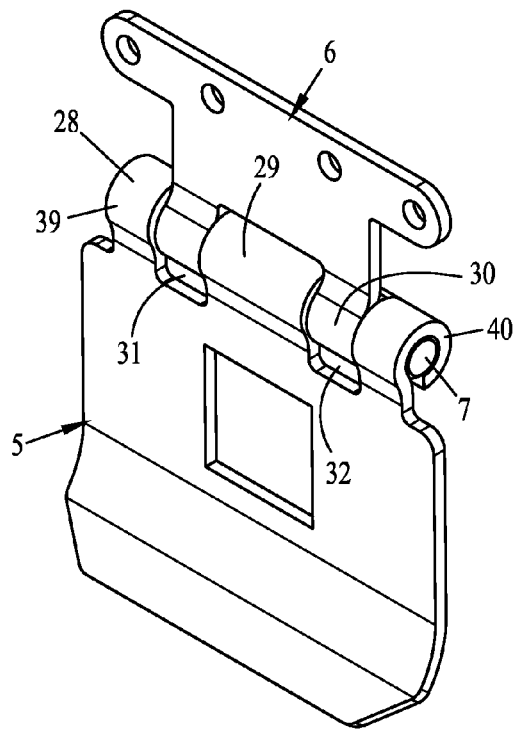
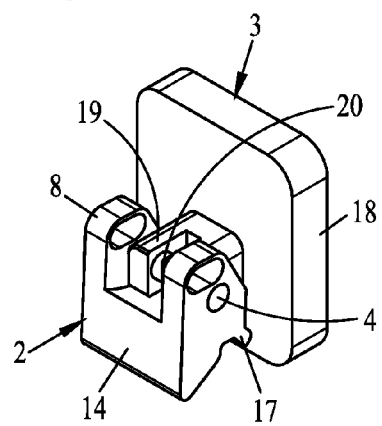

LOCK FOR STERILIZATION CONTAINER

CROSS REFERENCE TO RELATED APPLICATIONS

This application claims the benefit of priority under 35 U.S.C. §119 of German Utility Model Application 20 2011 104 615.3 filed Aug. 17, 2011, the entire contents of which are incorporated herein by reference.

FIELD OF THE INVENTION

The present invention pertains to a lock for locking a sterilization container comprising a container cover and a box-like bottom part, wherein the container cover and bottom part can be removed and placed airtightly on the bottom part and connected to same by means of a sealing means arranged peripherally between the container cover and bottom part to form a closed sterilization space, wherein the lock has a tensioning lever, which can be brought from a closed position located above dead center into an opened pivoted position pivotably about a pivot axis, and that a closing flap rotatable about an axis of rotation, which is in pulling connection with the tensioning lever in a positive-locking manner in its closed position, is provided.

BACKGROUND OF THE INVENTION

Locks for sterilization containers have already been known for years and are used to connect the container cover and the usually box-like bottom part of the sterilization container to one another detachably and tightly. In order to achieve as firm a hold of the container cover on the bottom part, locks of a lever-like design are used, among other things, which comprise a plurality of components, which can be caused to lockingly mesh with one another in the closed state. Another variant of locks operates according to the "toggle lever" principle, and such locks may be provided with a rocker arm and a clamping strap in the manner of a quick-acting lock.

A lock, which operates according to the "locking principle," is known from DE 197 55 532 A1. Furthermore, such locks are generally dealt with in that document. Thus, it is explained that the clamping together of the container cover and of the bottom part can be made possible by special locks, which have a pivotably mounted closing flap on one part (container cover or bottom part) and a stationarily fixed detent on the respective other part. The detent may be elastically deformable, so that a locking projection of the closing flap can snap into a locking recess of the detent during the pivoting motion of said closing flap. The detent is elastically deformed during the pivoting motion such that the locking projection can "slide into" the locking recess. The necessary tensioning force for bracing the container cover against the bottom part is determined by the elasticity of the detent.

Since certain difficulties arise in such constructions in connection with the compensation of manufacturing tolerances and the adaptation of the necessary tensioning force between the container cover and bottom part, it is proposed in the subject of DE 197 55 532 A1 that the locking projection in the flap be designed such that it is elastically displaceable in the closing flap. Corresponding to the dimensions of the closing flap, a relatively great path of displacement is available, which is substantially greater than the path of displacement of an elastically deformable detent. Adaptation to manufacturing tolerances is facilitated by this "enlarged" path of displacement. Furthermore, it is possible to vary the spring force with which the locking projection is displaced in the direction of the rebound.

If the locking projection is made in one piece with the closing flap, the elastic displaceability is achieved by elastically deformable connection members, which may be designed, for example, as spring-like webs or the like, being arranged in the connection area between the locking projection and the closing flap. Provisions are made in a preferred embodiment for the locking projection to be designed as a locking body, which is separate from the closing flap and is mounted displaceably in the flap in a guide. This embodiment is said to have the advantage of being able to be manufactured in an especially simple manner.

If was found in practice for such a lock that this is subject to increased wear because of the locking connection and also that the spring forces of the spring elements used weaken during a longer operating time, so that there is a risk that the container cover will be lifted off from the bottom part under higher internal pressures.

Furthermore, such locking locks are also known from U.S. Pat. No. 4,331,251 A. One of the locking elements, which can be caused to lockingly mesh with one another, is arranged elastically in a spring-loaded manner, for example, at the bottom part of the sterilization container, in this case as well. A hinged bolt, which is likewise provided with a detent, can extend lockingly behind this [the sterilization container], so that the sterilization container is thus closed.

A locking lock, which is designed as a "snap lock,", is known, in turn, from DE 721 588 C. A pivotable strap, which has an arc-shaped strap section, is provided in this construction. This strap section can be caused to lockingly engage a locking depression, for example, of the bottom part of the sterilization container.

Since such sterilization containers must be tight when the container cover is attached, the elastically resilient components must be designed as extremely stable components in the locking variants, so that the components that can be brought into locking connection with one another are subject to extremely great wear. If the locking forces that maintain the two components lockingly in connection with one another are too weak, there is a risk that the container cover is lifted off from the bottom part during the sterilization process and tightness is thus no longer guaranteed.

Furthermore, locks operating according to the toggle lever principle and above dead center principle are also known from the state of the art. A tensioning lever, which is mounted pivotably by means of a corresponding mount, for example, at the bottom part of the sterilization container, is provided in these locks. A tensioning strap is mounted pivotably at the tensioning lever at a certain distance from the mounting axis. When opening the tensioning lever, this clamping strap is moving away from the mounting axis of the tensioning lever and can thus be manually hung into a draw hook, which is in turn arranged fixed at the container cover. This draw hook is pulled during the closing operation in the direction of said mounting axis by the clamping strap due to the eccentric mounting of said clamping strap in relation to the mounting axis of the tensioning lever, so that the container cover can be braced against the bottom part. The pivot axis of the clamping strap according to the "above-dead-center principle" therefore lies in the fully closed state of the tensioning lever at the container wall of the bottom part as the mounting axis of the tensioning lever, so that independent opening of the tensioning lever is not possible.

The handling of such "classic" toggle lever locks is somewhat cumbersome, because the clamping strap freely movable at the tensioning lever must always be caused to mesh with the draw hook manually, especially for closing.

Further, various embodiment variants of container locks, which operate according to the above-dead-center principle, are known from U.S. Pat. No. 4,915,913 A. A tensioning lever, which is arranged pivotably at the container housing, is provided in one of these variants. A closing flap is arranged rotatably at the container cover. At its movable end, the closing flap has an end section bent off approximately semicylindrically towards the tensioning lever. The tensioning lever is provided with an opening, whose upper limiting edge directed in the closed state towards the closing flap has a likewise somewhat semicylindrically shaped meshing section. In the closed state, the end section of the closing flap passes through the tensioning lever and is in pulling connection with the meshing section of the tensioning lever. The positive-locking connection between the end edge of the closing flap and the meshing section of the tensioning lever is at a shorter distance in this closed state from the outer wall of the container housing than the axis of rotation of the closing flap and the pivot axis of the tensioning lever, so that a torque, which holds the tensioning lever and hence the container lock in the closed position, acts on the tensioning lever according to the above-dead-center principle. To open this lock, provisions are made for the tensioning lever to be deflected manually from its closed pivoted position. At the same time, a rotary motion of the closing flap is brought about by the pivoting motion of the tensioning lever brought about thereby via the positive-locking connection between the end section of the closing flap and the meshing section of the tensioning lever. The tensioning lever with its opening is moving during this pivoting motion of the tensioning lever along the closing flap, so that the latter passes through the opening over up to about half of its entire length. The closing flap is in contact with the meshing section of the tensioning lever in this opened position of the opening and is located with its end section under the meshing section. The meshing section and end section do not mesh with one another any longer in this position of the closing flap and tensioning lever. However, to make it nevertheless possible to lift off the container cover from the container housing, the closing flap must be brought manually from this half-opened position into a more widely opened position, while the tensioning lever must be maintained at the same time in its opened position. The adjusting motion of the closing flap is limited now by the opening of the tensioning lever. If the closing flap is in its maximally opened position, the tensioning lever must now be brought again into its closed position, so that the closing flap becomes unmeshed from the opening of the tensioning lever. It is only now that the container cover can be removed from the container housing. It can be seen that handling is extremely complicated in the case of this lock.

SUMMARY OF THE INVENTION

Accordingly, a basic object of the present invention is to design a lock for a sterilization container with a container cover and with a box-like bottom part (container housing) such that, in particular, simple handling is guaranteed, and the lowest possible wear shall be ensured.

This object is accomplished according to the present invention with a sterilization container comprising a container cover and a box-like bottom part, wherein the container cover and bottom part can be removed and placed airtightly on the bottom part and connected to same by means of a sealing means arranged peripherally between the container cover and bottom part to form a closed sterilization space, wherein the lock has a tensioning lever, which can be brought from a closed position located above dead center into an opened pivoted position pivotably about a pivot axis. A closing flap is rotatable about an axis of rotation, which is in pulling connection with the tensioning lever in a positive-locking manner in its closed position. The tensioning lever is able to be brought into its opened pivoted position by the closing flap via the positive-locking connection with the closing flap during the rotary motion of the closing flap from a closed position into an opened rotated position and by the closing flap becoming unmeshed (disengaged) from the tensioning lever after a further rotary motion into its fully opened end position. The tensioning lever is fixed in its opened pivoted position, and the closing flap meshes (engages) with the tensioning lever in a positive-locking manner during the closing operation. The tensioning lever is able to be adjusted by the closing flap into its closed tensioned position.

A lock with an extremely simple design as well as with extremely simple handling is made available by the design according to the present invention.

Provisions are made for the closing flap to mesh with a tensioning lever in the closed state under tensile stress. This tensioning lever can be brought pivotably from its closed tensioned position into an opened pivoted position. Based on the positive-locking connection between the closing flap and the tensioning lever in the closed state, the tensioning lever can be adjusted by the closing flap during the opening of the closing flap from its closed tensioned position into its opened pivoted position. If the closing flap is brought farther into its opened end position, it becomes unmeshed from the tensioning lever. The container cover can be lifted off from the box-like bottom part of the sterilization container in this position. In a correspondingly reversed direction, after placing the container cover on the bottom part, the closing flap is rotated manually from its opened end position into the closed position and will again mesh with the tensioning lever. The tensioning lever is fixed in its opened pivoted position for this purpose. Fixing may be brought about, for example, by a leg spring. Frictional engagement in the area of the pivoting mount of the tensioning lever or even a kind of locking connection are conceivable as well.

The tensioning lever is moved at the same time from its opened pivoted position into its closed tensioned position during the further closing motion due to the positive-locking connection formed between the closing flap and the tensioning lever. The tensioning lever is above dead center in relation to its pivot axis in this closed tensioned position, so that the tensioning lever and closing flap are inevitably fixed in this closed position. The lock according to the present invention can thus be actuated with one hand in a simple manner, and its components, which can be brought into functional connection with the one another, can be caused to mesh with one another and unmesh from one another automatically during the rotary motion of the closing flap.

Based on this positive-locking meshing and only a "rotating" relative motion of the closing flap relative to the tensioning lever in the area of the positive-locking connection, the closing flap and tensioning lever are subject to an extremely low wear only.

Furthermore, extremely strong closing forces can be applied due to the special design of the lock to the sealing means, which are usually provided between the container cover and the bottom part, so that lifting off of the container cover from the bottom part and thus the development of a leak are prevented from occurring with certainty in case of an internal overpressure within the sterilization container. Since no springy elements are provided in this solution according to the present invention, there also is no risk that the closing or tensioning forces would decrease with increasing operating time.

Thus, provisions may be made according to another aspect of the invention for the tensioning lever to be of a block-like design and have two mounting legs, which are spaced apart from each other and each of which is provided with a mounting hole. The tensioning lever is mounted pivotably via these mounting legs at a mounting block fastened to the sterilization container. Great stability of the tensioning lever is achieved due to this embodiment. Furthermore, a leg spring, by which the tensioning lever is held in its opened pivoted position not meshing with the closing flap, may be arranged between the two mounting legs.

Furthermore, provisions may be made according to another aspect of the invention for the tensioning lever to form a clamping block starting from the mounting legs and for the clamping block to have, in its end area located opposite the mounting legs, a depression, which extends in parallel to its pivot axis and with which the closing flap can be caused to mesh in a positive-locking and movable manner. The closing flap and tensioning lever can be caused to mesh with one another with certainty due to this embodiment.

The embodiment according to another aspect of the invention also contributes to reliable operation. Provisions are made according to this embodiment for the depression to be limited on the "rear side" towards the sterilization container by a stop web extending approximately radially in relation to the pivot axis, which said stop web comes into functional connection with the closing flap during the closing operation, and a meshing surface to adjoin the depression opposite the stop web. The stop web may act here not only as a stop for the closing flap, but it may also define the closed tensioned position of the tensioning lever by this web being in contact in the closed tensioned position, for example, with the sterilization container and with a component located on the outside of the sterilization container.

The embodiments according to other aspects of the invention are provided to make it possible to mesh the closing flap with the tensioning lever in a "reliable operation" and to detach the closing flap from the tensioning lever again in a simple manner.

Thus, provisions may be made for the closing flap to be mounted rotatably on the sterilization container via a mounting element and for the closing flap to have a central opening with a meshing strip, which extends in parallel to the axis of rotation and can be caused to mesh with the tensioning lever in a positive-locking manner.

Provisions may also be made for the tensioning lever with its clamping block to pass through the opening of the closing flap in the closed state of the lock and for the opening to form a meshing strip, which meshes with the depression of the clamping block in a positive-locking manner and rotatably relative hereto in the closed state of the lock.

The principle of operation of the lock according to the present invention will be explained in more detail as an example on the basis of the drawings. The components shown are only examples here and their construction may also be designed differently. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

FIG. 1 is perspective exploded view of a possible embodiment variant of a lock according to the present invention;

FIG. 2 is perspective view of the closing flap in its state in which it is received rotatably in a mounting element;

FIG. 3 is perspective view of the tensioning lever in its state in which it is mounted pivotably on a mounting block;

DESCRIPTION OF THE PREFERRED EMBODIMENTS

Figure 4:
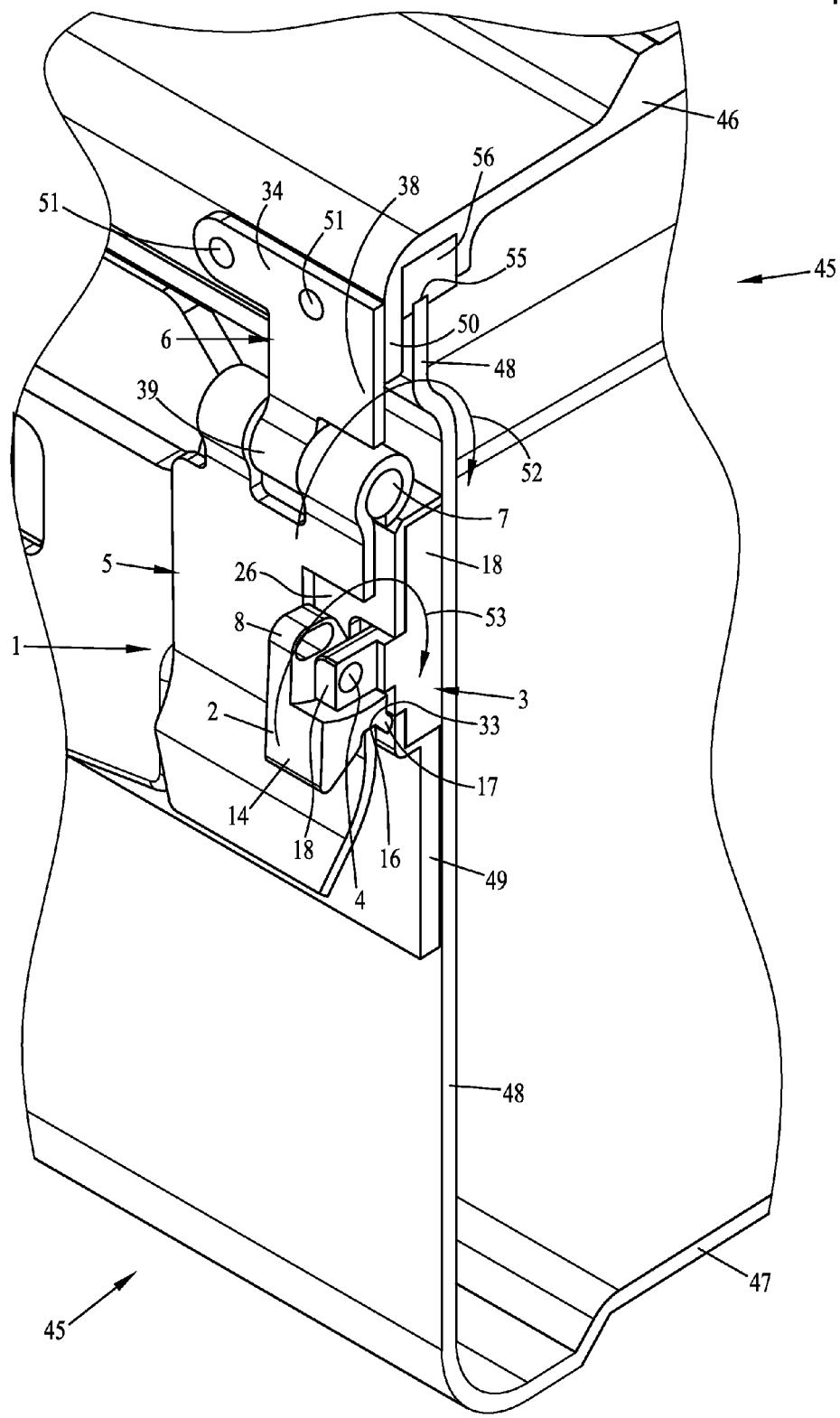
FIG. 4 is partial perspective view of a sterilization container with container cover and box-like bottom part with a lock according to the present invention in the closed state thereof.

Referring to the drawings in particular, FIG. 1 shows a perspective exploded view of a possible embodiment variant of the components of a lock 1 according to the present invention. This lock 1 comprises a tensioning lever 2 and a corresponding clamping block 3, on which the tensioning lever 2 is mounted pivotably during the operation via a pivot axis 4. Furthermore, a closing flap 5 is provided, which is mounted rotatably during use at a mounting element 6 via an axis of rotation 7.

Tensioning lever 2 is of a block-like design in the embodiment variant shown and has two vertically upwardly directed mounting legs 8 and 9. In its upper end area, each of the mounting legs 8, 9 is provided with a respective elongated hole 10 and 11, which are used to secure the position of the tensioning lever 2 in the closed tensioned position thereof during the operation. Mounting holes 12 and 13, via which the tensioning lever can be received pivotably at the mounting block 3, are provided in the two mounting legs 8 and 9 below these elongated holes 10 and 11.

Furthermore, it is seen in FIG. 1 that under its mounting holes 12 and 13 or under its two mounting legs 8 and 9, the tensioning lever 2 forms a clamping block 14, which forms an obliquely extending meshing (engaging) surface 15 on the rear side towards the mounting block 3. Below the two mounting holes 12 and 13, this meshing surface 15 opens into a groove-like depression 16, which is limited on the rear side, towards the mounting block 3, by a projecting stop web 17 extending downwardly and obliquely rearwardly, approximately radially to the two mounting holes 12 and 13.

Mounting block 3 has a plate-like design in the embodiment variant shown and correspondingly has a mounting plate 18, which is provided on the front side with two mounting tongues 19 and 20 projecting towards the tensioning lever 2. Each of these respective mounting tongues 19 and 20 is provided with a through hole 21 and 22, respectively, which are used to pivotably mount the tensioning lever 2 via the pivot axis 4. The two mounting tongues 19 and 20 can be pushed fittingly in between the two mounting legs 8 and 9 of the tensioning lever 2, so that the tensioning lever 2 is received pivotably by the mounting tongues 19 and 20 with little clearance in the mounted state. The two mounting tongues 19 and 20 form between them, in the area of the through holes 21 and 22, a milled recess 23, with which a leg spring can be inserted to fix the opened pivoted position of the tensioning lever 2 relative to the mounting block 3 (not shown in the drawing).

As can be seen in FIG. 1, the closing flap 5 is of a plate-like design in the exemplary embodiment shown and has a flat bolt section 25, which is provided with a rectangular opening 26. An actuating strip 27, which is bent forward on the outside and can be grasped behind manually during use, so that the closing flap 5 can be especially opened in an extremely simple manner via this actuating strip 27, is made integrally in one piece on the bolt section 25 below said opening 26. Three bearing eyes 28, 29 and 30 are made integrally in one piece with the bolt section 25 above the latter. A respective mounting area 31 and 32 is formed between the two outer bearing eyes 28 and 30 and the middle bearing eye 29. The closing flap is mounted rotatably on the mounting element 6 via the axis of rotation 7 during the operation via these bearing eyes 28, 29 and 30.

The dimensions of the rectangular opening 26 are selected to be such that the tensioning lever 2 with its clamping block 14 can be passed through opening 26 in the opened pivoted position of tensioning lever 2. This opening 26 forms with its lower edge a meshing (engaging) strip 33, which can be closed to mesh with the groove-like depression 16 in the tensioning lever 2 in a positive-locking manner during the operation, especially in the closed state of lock 1.

In its upper end area, the mounting element 6 has a kind of bearing web 34, which forms two laterally projecting mounting tongues 35 and 36. This bearing web 34 is provided in this exemplary embodiment with a total of four mounting holes 37, via which the mounting element 6 can be mounted in a fixed manner, for example, in the edge area of a container cover. Under the bearing web 34, mounting element 6 forms a connection section 38, with which two bearing eyes 39, 40 projecting downwardly towards the closing flap 5 are made integrally in one piece. The distance of these bearing eyes 39 and 40 as well the width thereof are selected to be such that these bearing eyes 39 and 40 can be inserted with little clearance into the two mounting areas 31 and 32 of the three bearing eyes 28, 29 and 30 of the closing flap 5. The closing flap 5 can thus be coupled in this mounted state rotatably with the mounting element 6 via the axis of rotation 7.

This mounted state is shown in FIG. 2 in a perspective view. It can be seen that the two bearing eyes 39 and 40 of mounting element 6 are inserted into the two mounting areas 31 and 32 between the bearing eyes 28 and 29 or 29 and 30 of the closing flap 5. The axis of rotation 7 is passed through all bearing eyes 28, 29, 30 and 39, 40. To secure this connection position, the bearing eyes 28, 29, 30 and/or 39, 40 may be under radial prestress, so that the axis of rotation 7 is held clampingly in the bearing eyes 28 through 30 and 29, 40. The closing flap 5 is approximately in its closed closing position in the relative rotated position shown in FIG. 6.

FIG. 3 shows a perspective view of the tensioning lever 2 mounted on mounting block 3. The two mounting tongues 19 and 20 of mounting block 3 are inserted between the two mounting legs 8 and 9 of tensioning lever 2, so that tensioning lever 2 is received pivotably at the mounting block 3 via the pivot axis 4. FIG. 3 likewise shows a relative pivoted position of tensioning lever 2 relative to the mounting block 3, in which position tensioning lever 2 is approximately in its closed tensioned position. In this tensioned position, tensioning lever 2 is in contact with its stop web 17 projecting downwardly and towards the mounting plate 18 on the outside with the mounting plate 18. This stop web 17 thus forms at the same time a defined stop for fixing the "closed" tensioned position of tensioning lever 2.

FIG. 4 shows a partially perspective sectional view of a sterilization container 45, which has an upper container cover 46 as well as a box-like bottom part 47. The front limiting wall 48 of the bottom part 47 can be seen as an example in a partial perspective view in FIG. 4. Mounting block 3 is mounted stationarily at this limiting wall 48. On the one hand, the mounting plate 18, with which the mounting block 3 is flatly in contact with the front limiting wall, can be seen from this mounting block 3 in this perspective partial section shown in FIG. 4. Mounting block 3 may be screwed on the rear side to the limiting wall 48 or fastened to the limiting wall 48 via a separate, multiply bent holding plate 49. Mounting block 3 is not screwed to the limiting wall 48 in this exemplary embodiment, so that the side wall 48 does not have to be provided with through holes and thus there is no risk of "becoming leaky." The "holding plate" 49 may also be designed as a milled part made of aluminum and pressed together with the side wall 48 according to a special process.

FIG. 4 shows, furthermore, the outwardly projecting mounting tongue 19 as well as the mounted pivot axis 4. Tensioning lever 2 with its mounting leg 8 is mounted pivotably on this pivot axis 4 and is in its closed tensioned position in FIG. 4. It can be seen that stop web 17 is in contact on the outside with a part of the mounting plate 49 in this embodiment variant. Mounting element 6 with its bearing web 34 is arranged stationarily at a vertically downwardly extending web wall 50 of the container cover 46. Screws or, as is shown, fastening rivets 51 may be provided here for the stationary connection. Mounting element 6 is likewise directed vertically corresponding to the vertical orientation of web wall 50 with a connection section 38 and is located with its bearing eye 39 in the upper end area in front of the front limiting wall 48.

The vertically downwardly directed closing flap 5 meshes with the tensioning lever 2 in a positive-locking manner. It can be seen that the meshing strip 33 of opening 26 meshes with the depression 16 of the tensioning lever 2 or the clamping strap 14 thereof in a positive-locking manner. Depression 16 and meshing strip 33 are offset towards the limiting wall 48 in this closed position of the lock 1, so that this meshing area is located between tensioning lever 2 and closing flap 5 above dead center of the tensioning lever 2 in this closed position of lock 1. Due to this design, the tensioning lever 2 is correspondingly held automatically in its tensioned position shown in FIG. 4.

If the closing flap 5 is now rotated about the axis of rotation 7 in the direction of arrow 52, a pivoting motion of tensioning lever 2 in the direction of arrow 53 about the pivot axis 4 is likewise brought about. This is based on the positive-locking meshing of the meshing strip 33 of the closing flap 5 with depression 16 of the clamping strap 14. Tensioning lever 2 is thus inevitably brought during the opening of the closing flap 5 from the tensioned position shown in FIG. 4 into an opened position beyond dead center into an opened pivoted position [sic-Tr.Ed.].

Figure 5:
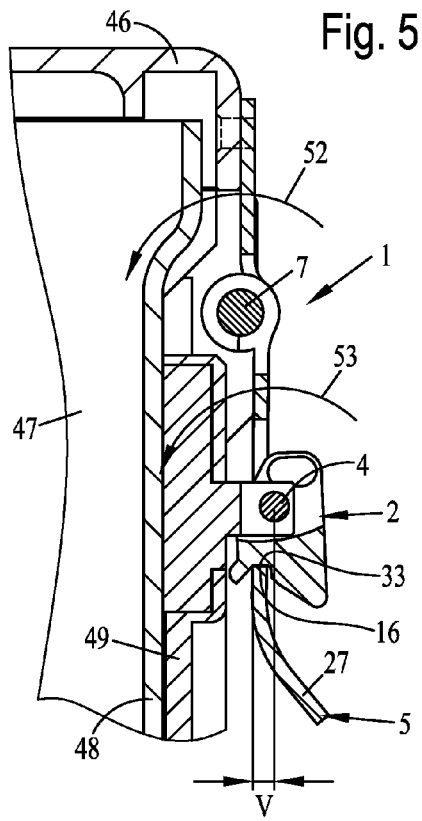
FIG. 5 is sectional view of the sterilization container from FIG. 4 with the lock according to the present invention in the closed state.
Figure 6:
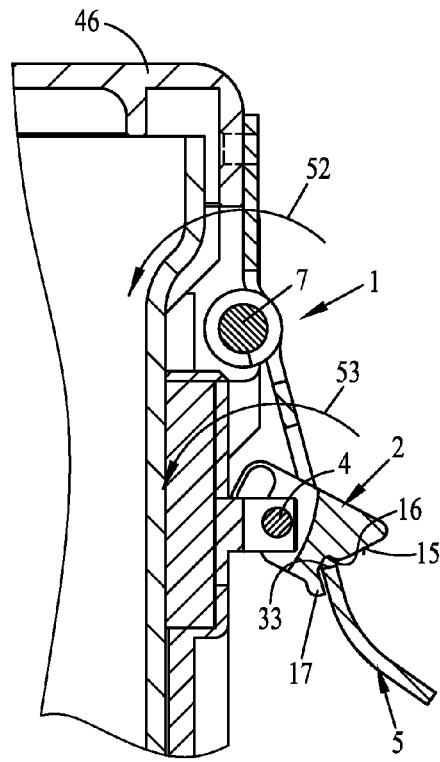
FIG. 6 is the view from FIG. 5 with the lock in its partially opened operating position.
Figure 7:
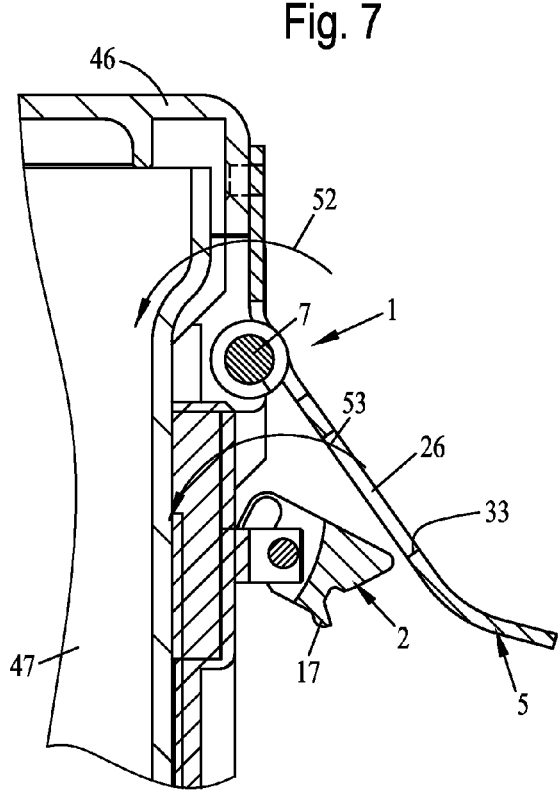
FIG. 7 is the view from FIG. 6 with the lock in its opened operating position.

FIGS. 5, 6 and 7 show for this the corresponding motion processes. It shall also be mentioned in this connection that a sealing element 56, which is under elastic prestress with the bottom part 47 in this closed, braced state of the container cover 46, may be arranged between the upper edge 55 and the container cover 46.

FIG. 5 shows a partial sectional view of container cover 46 in the state in which it is mounted on the bottom part 47 with the mounted lock 1 in its closed position, as this was already described in connection with FIG. 4.

In particular, it can be seen from FIG. 5 that the meshing strip 33 together with the depression 16 is offset by an offset v relative to the pivot axis 4 towards the limiting wall 48. Based on this "above-dead-center arrangement," a torque is applied against the direction of arrow 53 because of the existing tensile forces brought about, for example, by the elastic sealing element 56, which act on the lock in this closed position, so that tensioning lever 2 is held under prestress in the tensioned position shown. Based on the positive-locking meshing of the meshing strip 33 with depression 16, the closing flap 5 is also held correspondingly at the same time in its closed position shown. The "rear" stop web 17 is in contact with a part of mounting plate 49 in this embodiment variant shown, so that this tensioned position of tensioning lever 2 or the closed position of the closing flap 5 is exactly defined. To open lock 1, opening of the lock 1 can now be brought about by actuating the closing flap 5 in the area of the actuating strip 27 thereof in the direction of arrow 52.

FIG. 6 shows for this an intermediate position, in which the closing flap 5 was opened in the direction of arrow 52 to the extent that the tensioning lever 2 has reached its opened pivoted position in the direction of arrow 53. Tensioning lever 2 can be held in this pivoted position securely, for example, by a leg spring arranged in the area of pivot axis 4. This opened pivoted position of tensioning lever 2 can now be fixed by a special shape of tensioning lever 2, so that this cannot be moved farther in the direction of arrow 53.

Furthermore, it can be seen from FIG. 6 as a suggestion that the meshing strip 33 is located now approximately in the "circumferential area" of the meshing surface 15. Thus, meshing strip 33 does not mesh with depression 16 of the tensioning lever 2 any longer. By rotating the closing flap 5 farther in the direction of arrow 52, closing flap 5 with its opening 26 or the meshing strip 33 will thus fully unmesh with the tensioning lever 2, as this can be seen in FIG. 7. The container cover 46 can be lifted off from the bottom part 47 in this opened position.

During a corresponding closing motion against arrow 52 from the pivoted position of the closing flap 5 shown in FIG. 7, bolt section 25 with its meshing strip 33 will again mesh with the stop web 17 of tensioning lever 2 in a positive-locking manner as soon as the closing flap 5 is in the position shown in FIG. 6. Tensioning lever 2 is thus moved back into its closed tensioned position shown in FIG. 5 via the stop web 17 by rotating the closing flap 5 farther against arrow 52.

It can be seen especially from FIGS. 5 through 7 that the lock 1 according to the present invention can be actuated in an especially simple and reliable manner. No components whatsoever need to be suspended, especially before the closing operation. It is also unnecessary to remove two or more functional components during opening. Extremely simple handling of the lock 1 is thus guaranteed by the design according to the present invention.

Furthermore, it is also possible to apply extremely strong tensioning forces to close the container cover 46 on the bottom part 47. In particular, lifting off of the container cover 46 from the bottom part 47 and hence the sterilization container "developing a leak" are ruled out with certainty in the closed operating position of lock 1.

Since the meshing strip 33 performs only a relatively small "rotating" relative motion relative to the depression 16 during the opening and closing, relatively low wear is achieved as well.

While specific embodiments of the invention have been shown and described in detail to illustrate the application of the principles of the invention, it will be understood that the invention may be embodied otherwise without departing from such principles.

What is claimed is:

1. A lock for locking a sterilization container comprising a container cover, a bottom part, wherein the container cover can be removed and can be placed airtightly on the bottom part and a sealing means, said container cover being connected to said bottom part by means of said sealing means arranged peripherally between said container cover and said bottom part to form a closed sterilization space, the lock comprising:

a tensioning lever which can be brought, pivotably about a pivot axis, from a closed tensioned position located above dead center into an opened pivoted position;

a closing flap rotatable about an axis of rotation, said closing flap being in pulling connection with the tensioning lever in a positive-locking manner in a closing flap closed position, wherein:

said tensioning lever is brought by the closing flap into said opened pivoted position via a positive-locking connection with said closing flap during a rotary motion of said closing flap from said closing flap closed position into a closing flap opened rotated position, and said closing flap disengages with the tensioning lever after a further rotary motion into a closing flap fully opened position;

said tensioning lever is fixed in said opened pivoted position, and said closing flap engages with said tensioning lever in a positive-locking manner during closing and said tensioning lever is adjusted by said closing flap into said closed tensioned position; and said tensioning lever comprises a block and two mounting legs located at spaced locations from one another and provided with a mounting hole each, said tensioning lever being mounted pivotably on a mounting block fastened to the sterilization container.

2. A lock in accordance with claim 1, wherein:

said tensioning lever forms a clamping block starting from said mounting legs, said clamping block having an end area located opposite said mounting legs, a depression extending in parallel to a pivot axis; and said closing flap is caused to engage in a positive-locking and movable manner.

3. A lock in accordance with claim 2, wherein said depression is limited on a rear side towards the sterilization container by a stop web extending approximately radially to said pivot axis, said web coming into functional connection with said closing flap during a closing operation, and said depression being joined by an engaging surface opposite to a stop web.

4. A lock in accordance with claim 1, wherein:

said closing flap is mounted rotatably on the sterilization container via a mounting element; and said closing flap has a central opening with an engaging strip extending in parallel to said axis of rotation, with said engaging strip, said closing flap being caused to engage with said tensioning lever in a positive-locking manner.

5. A lock in accordance with claim 4, wherein:

said tensioning lever with said clamping block passes through said central opening of said closing flap in the closed state of lock; and said central opening forms said engaging strip for engaging with said depression of said clamping block in a positive-locking manner and rotatably in relation thereto in the closed state of the lock.

6. A lock and sterilization container comprising:
a container cover;
a bottom part, wherein said container cover can be removed and can be placed airtightly on said bottom part;
a sealing means, said container cover being connected to said bottom part by means of said sealing means arranged peripherally between said container cover and said bottom part for forming a closed sterilization space; and
a lock comprising:
a tensioning lever which can be brought, pivotably about a pivot axis, from a closed tensioned position located above dead center into an opened pivoted position;
a closing flap rotatable about an axis of rotation, said closing flap being in pulling connection with the tensioning lever in a positive-locking manner in a closing flap closed position, wherein said tensioning lever is brought by the closing flap into said opened pivoted position via a positive-locking connection with said closing flap during a rotary motion of said closing flap from said closing flap closed position into a closing flap opened rotated position, and said closing flap disengages with the tensioning lever after a further rotary motion into a closing flap fully opened position and said tensioning lever is fixed in said opened pivoted position, and said closing flap engages with said tensioning lever in a positive-locking manner during closing and said tensioning lever is adjusted by said closing flap into said closed tensioned position, said tensioning lever comprising a block and two mounting legs located at spaced locations from one another and provided with a mounting hole each, said tensioning lever being mounted pivotably on a mounting block fastened to the sterilization container.

7. A lock and sterilization container in accordance with claim 6, wherein:
said tensioning lever forms a clamping block starting from said mounting legs, said clamping block having an end area located opposite said mounting legs, a depression extending in parallel to a pivot axis; and
said closing flap is caused to engage in a positive-locking and movable manner.

8. A lock and sterilization container in accordance with claim 7, wherein said depression is limited on a rear side towards the sterilization container by a stop web extending approximately radially to said pivot axis, said web coming into functional connection with said closing flap during a closing operation, and said depression being joined by an engaging surface opposite to a stop web.

9. A lock and sterilization container in accordance with claim 6, further comprising via a mounting element wherein:
said closing flap is mounted rotatably on the sterilization container via said mounting element; and
said closing flap has a central opening with an engaging strip extending in parallel to said axis of rotation, with said engaging strip, said closing flap being caused to engage with said tensioning lever in a positive-locking manner.

10. A lock and sterilization container in accordance with claim 9, wherein:
said tensioning lever with said clamping block passes through said central opening of said closing flap in the closed state of lock; and
said central opening forms said engaging strip for engaging with said depression of said clamping block in a positive-locking manner and rotatably in relation thereto in the closed state of the lock.

* * * * *